United States Patent
Straub et al.

(10) Patent No.: US 11,975,107 B2
(45) Date of Patent: *May 7, 2024

(54) COMPOSITIONS AND RESULTING HARD CAPSULES COMPRISING HYDROPHILIC COLORING FOODSTUFF CONCENTRATES

(71) Applicant: Capsugel Belgium NV, Bornem (BE)

(72) Inventors: Hugues Straub, Colmar (FR); Stefaan Jaak Vanquickenborne, Rijmenam (BE)

(73) Assignee: Capsugel Belgium NV, Bornem (BE)

( * ) Notice: Subject to any disclaimer, the term of this patent is extended or adjusted under 35 U.S.C. 154(b) by 0 days.

This patent is subject to a terminal disclaimer.

(21) Appl. No.: 17/856,682

(22) Filed: Jul. 1, 2022

(65) Prior Publication Data

US 2022/0339113 A1    Oct. 27, 2022

Related U.S. Application Data

(63) Continuation of application No. 16/789,701, filed on Feb. 13, 2020, now Pat. No. 11,406,601, which is a continuation of application No. 16/070,499, filed as application No. PCT/IB2016/058123 on Dec. 30, 2016, now Pat. No. 10,603,286.

(30) Foreign Application Priority Data

Jan. 28, 2016   (EP) ..................................... 16153238
Jan. 29, 2016   (EP) ..................................... 16153306

(51) Int. Cl.

| | |
|---|---|
| A61K 9/48 | (2006.01) |
| A23P 10/30 | (2016.01) |
| A23P 30/10 | (2016.01) |
| B29C 41/00 | (2006.01) |
| B29C 41/14 | (2006.01) |
| B29K 1/00 | (2006.01) |
| B29K 105/00 | (2006.01) |
| B29L 31/00 | (2006.01) |

(52) U.S. Cl.
CPC ............ *A61K 9/4816* (2013.01); *A23P 10/30* (2016.08); *A23P 30/10* (2016.08); *A61K 9/4808* (2013.01); *A61K 9/4883* (2013.01); *B29C 41/003* (2013.01); *B29C 41/14* (2013.01); *B29K 2001/08* (2013.01); *B29K 2105/0032* (2013.01); *B29K 2995/0092* (2013.01); *B29L 2031/7174* (2013.01)

(58) Field of Classification Search
CPC .. A61K 9/4816; A61K 9/4808; A61K 9/4883; A23P 10/30; A23P 30/10; B29K 2001/08; B29K 2105/0032; B29K 2995/0092; B29L 2031/7174; B29C 41/003
See application file for complete search history.

(56) References Cited

U.S. PATENT DOCUMENTS

| | | | |
|---|---|---|---|
| 4,539,060 A | 9/1985 | Wittwer et al. | |
| 4,656,066 A | 4/1987 | Wittwer | |
| 10,603,286 B2* | 3/2020 | Straub ..................... | B29C 41/14 |
| 11,406,601 B2* | 8/2022 | Straub .................. | A61K 9/4816 |
| 2005/0249676 A1* | 11/2005 | Scott ..................... | A61K 9/4816 |
| | | | 424/46 |
| 2007/0087939 A1* | 4/2007 | Cade ......................... | C08L 1/26 |
| | | | 536/123 |
| 2008/0248102 A1* | 10/2008 | Rajewski ............. | A61K 9/4816 |
| | | | 514/777 |
| 2013/0295188 A1* | 11/2013 | Cade ...................... | A61K 47/10 |
| | | | 424/494 |
| 2015/0140084 A1 | 5/2015 | Takubo | |
| 2015/0150817 A1 | 6/2015 | Hoelzer | |

FOREIGN PATENT DOCUMENTS

| | | | |
|---|---|---|---|
| BR | 112018014719 | 12/2018 | |
| CA | 3011656 | 8/2017 | |
| CN | 102578450 | 7/2012 | |
| CN | 103509369 A | 1/2014 | |
| EP | 0110500 | 6/1984 | |
| EP | 0387739 | 9/1990 | |
| EP | 1358875 A1 | 5/2003 | |
| EP | 1358875 A1 * | 11/2003 | ............... A61J 3/07 |
| EP | 1849461 A1 | 10/2007 | |
| EP | 3199148 A1 | 8/2017 | |
| JP | H04193825 A | 7/1992 | |
| JP | 2003321619 A | 11/2003 | |
| JP | 2006016372 A | 1/2006 | |
| JP | 2006096678 A | 4/2006 | |
| JP | 2007091670 A | 4/2007 | |
| JP | 2009524573 A | 7/2009 | |
| JP | 2013528209 A | 7/2013 | |
| JP | 2019503690 A | 2/2019 | |
| WO | WO03/092663 A1 | 11/2003 | |
| WO | WO2014/023712 A1 | 2/2014 | |

OTHER PUBLICATIONS

Allam, Krishna Vamshi et al., "Colorants—The Cosmetics for the Pharmaceutical Dosage Forms," *International Journal of Pharmacy and Pharmaceutical Sciences*, 3(Suppl 3):13-21 (Jan. 2011).
Akhtar, Muhammad Javeed, "Functionalization and Characterization of Bioactive Films Based on HPMC: Influence of Antioxidants V Inclusion on Films Properties and Food Preservation, Food and Nutrition. Universite de Lorraine, 2012," pp. 1-203, 2012 (Year: 2012) (submitted Mar. 29, 2018).
Anonymous, "Capsugel List of Colorants for Oral Drugs 2002," 11th Edition, 24 pp. (2002).
Commission Regulation (EU) No. 231/2012 of Mar. 9, 2012, *Official Journal of the European Union*, Mar. 22, 2021, 295 pages.
Crane, Michaels, "Spirulina Extract Gets FDA Approval for Coloring of Tablet and Capsule Coatings," *Nutritional Outlook*, http://www.nutritionaloutlook.com/delivery-systems/spirulina-extract-gets-fda-approval-coloring-tablet-and-capsule-coatings (Sep. 3, 2015).

(Continued)

*Primary Examiner* — Blessing M Fubara
(74) *Attorney, Agent, or Firm* — Klarquist Sparkman, LLP

(57) ABSTRACT

An aqueous composition for making dip-molded comestible hard capsules comprising a film forming capsule base material and one or more colorants each consisting of a hydrophilic coloring foodstuff concentrate.

20 Claims, No Drawings

(56) References Cited

OTHER PUBLICATIONS

EU Guidance Notes on the Classification of Food Extracts with Colouring Properties, Version 1, Nov. 29, 2013, 18 pages.
Extended Search Report for European Patent Application No. 16153306.2 (dated Feb. 8, 2017).
International Search Report and Written Opinion for PCT/IB2016/058123 (dated Jun. 21, 2017).
Office Action for European Patent Application No. 16153306.2 (dated Oct. 12, 2018).
Office Action for Japanese Patent Application No. 2018-537776 (dated Sep. 14, 2020) (w/English translation).
Office Action for Brazilian Patent Application No. 112018014719 (dated Oct. 7, 2020) (w/informal translation).
Office Action for Japanese Patent Application No. 2018-537776 (dated Jan. 12, 2021) (w/English translation).
Partial Search Report for European Patent Application No. 16153306.2 (dated Sep. 23, 2016).
Regulation (EC) No. 1333/2008 of the European Parliament and the Council of Dec. 16, 2008 on food additives, *Official Journal of the European Union*, Dec. 21, 2008, 18 pages.
RU 2420538 C2 (using the PE2E translated document), Kad Dominik Nikolja et al., Jun. 10, 2011.
Search Report for Japanese Patent Application No. 2018-537776 (dated Aug. 27, 2020) (w/English translation).

\* cited by examiner

COMPOSITIONS AND RESULTING HARD CAPSULES COMPRISING HYDROPHILIC COLORING FOODSTUFF CONCENTRATES

CROSS REFERENCE TO RELATED APPLICATIONS

This is a continuation of U.S. application Ser. No. 16/789,701, filed on Feb. 13, 2020, which is a continuation of U.S. patent application Ser. No. 16/070,499, filed on Jul. 16, 2018, now U.S. Pat. No. 10,603,286, which is the U.S. National Stage of International Application No. PCT/IB2016/058123, filed Dec. 30, 2016, which was published in English under PCT Article 21(2), which in turn claims the benefit of European Patent Application No. 16153238.7, filed Jan. 28, 2016, and European Patent Application No. 16153306.2, filed Jan. 29, 2016, which are all incorporated herein in their entireties.

FIELD

The present disclosure relates to compositions and resulting dosage form articles for the delivery of one or more drugs/medicaments (or health and nutrition materials) via oral, vaginal, rectal or other, administration of the same to a subject. More particularly, the dosage form articles are comestible and suitable for assimilation by a subject, preferably the subject being selected from humans or animals.

The compositions and resulting capsules comprising one or more colorants each consisting of hydrophilic coloring foodstuff concentrates.

BACKGROUND

Receptacle technology, and in particular capsule technology, continues to be subject to development and improvements and so does the manufacture thereof, including processes and equipment. In its basic form, standard containers for pharmaceuticals or other powdered, granular or liquid substances (generally referred to as telescope-type or two-piece capsules) include a tubular-shaped and/or cylindrically-shaped first part, namely a cap part, which is closed on one end and open on the other opposite end. A tightly fitting second part of similar shape, namely the body part, is of smaller diameter than the cap part and is typically telescopically engaged therein to form the overall dosage form or two-piece capsule. Similar capsule technology may be used to generate multi-compartment capsules.

Capsules generally comprise or are made of functional base shell materials (most commonly gelatin, but in more recent times also alternate polymers such as celluloses or pullulan) and other additives such as gelling agents, plasticizers and/or colorants.

In particular colorants have been typically employed specifically to provide a vast sweet of color options for capsules and thus purely for providing an aesthetic appearance sometimes linked to the branding of the ultimate dosage form. Such colorants are commonly synthetically derived colorants or selectively extracted pigments from natural sources since typically such materials tend to experience lesser fading with time as well as particular resistance to thermal degradation.

Nevertheless, there is a desire for introduction of natural colorants in hard capsules, however this poses several challenges which have limited their use in favor of synthetically derived or extracted colorants and pigments.

There is a desire to provide hard capsule compositions that contain truly natural colorants that provide for good physical and color stability as well as added functionality and/or improved compatibility with aqueous based gelling systems used specifically in hard capsule manufacture.

There is further a desire for colorants that allow their incorporation in capsule making compositions without further dispersion prior to mixing therewith.

SUMMARY

A first aspect of the present disclosure relates to an aqueous composition for making dip-molded comestible hard capsules comprising a film forming capsule base material and one or more colorants wherein each said colorant consists of a hydrophilic coloring foodstuff concentrate.

A further aspect of the present disclosure relates to a two-piece hard capsule, the capsule comprising a film forming capsule base material and one or more colorants wherein each said colorant consists of a hydrophilic coloring foodstuff concentrate.

A further aspect of the present disclosure relates to a dip-molding process for making two-piece hard capsules comprising the steps of: providing an aqueous composition comprising a film forming capsule base material; directly mixing one or more colorants each consisting of hydrophilic coloring foodstuff concentrates with said aqueous composition to provide a dipping composition; dipping one or more mold pins in said dipping composition; extracting said one or more mold pins from said dipping composition such that a film is formed over said pins; and drying said films to provide capsule shells.

A further aspect of the present disclosure relates to the use of one or more colorants, each said colorant consisting of a hydrophilic coloring foodstuff concentrate, in hard capsules, typically to provide a color and a functional attribute to said capsule, said functional attribute being selected from the group consisting of aromatic, sapid or nutritive properties

DETAILED DESCRIPTION

By the term "a" and/or "an" when describing a particular element, it is intended "at least one" of that particular element.

By the term "medicament", it is intended a "drug" or the like comprising one or more compounds providing one or more curative benefits to a subject, the terms "medicament" and "drug" may be used interchangeably herein.

By the term "hard shell" or "hard capsule shell", it is intended a shell that is deformable, but which substantially returns to its un-deformed shape upon the removal of a deforming force. Typically such shells comprise less than 25%, preferably less than 20%, more preferably from 0% to 14%, even more preferably from greater than 0% to less than 14%, water by weight.

In the present disclosure, if not otherwise indicated, by "capsule" it is meant a hard capsule consisting of two co-axial, telescopically-joined parts, referred to as body and cap.

By the term "coloring foodstuff concentrate", it is intended a concentrate from a source material consisting of food or a characteristic ingredient of food, and wherein the source material does not undergo selective physical and/or chemical extraction. Rather, the source material is typically concentrated by traditional grinding/squeezing, dilution with non-organic solvent additives (such as water, sugars such as inverted sugar (a non-crystalline version of sucrose)

or D-Trehalose, and citric acid (or derivatives thereof, like trisodium citrate), followed by drying/evaporation (at temperatures not exceeding 240° C.). Typically such coloring foodstuff concentrate having an enrichment factor Fe (also referred to as Fn) of less than 6.

By the term "directly mixing", it is intended mixing directly in the element referred to (e.g. a composition) without further dilution or solubilization or other pre-mixing with further materials.

The term "relative humidity" is used herein to mean the ratio of the actual water vapor pressure at a given temperature to the vapor pressure that would occur if the air were saturated at the same temperature. There are many technologies for humidity measurement instruments known to the skilled person, all of which would give substantially the same RH measure.

By the term "hydrophilic", it is intended that the material referred to has strong affinity with water in that they form a solution when added to water without phase splitting (or forming separate phases) generally due to the material charge-polarized characteristics and capability of hydrogen bonding.

By the term "carbohydrates", it is intended mono- and oligo-saccharides only. Various embodiments will now be described to provide an overall understanding of the principles of the structure, function, manufacture, and use of dosage forms, uses, and methods disclosed herein. One or more examples of these embodiments are illustrated in the accompanying figures. Those of ordinary skill in the art will immediately understand that features described or illustrated in connection with one example embodiment can be combined with the features of other example embodiments without generalization from the present disclosure.

The Composition

Compositions herein for making hard capsules comprise, preferably consist essentially of, a film forming capsule base material, one or more colorants and water. Optionally, one or more further additives may be comprised such as plasticizers, anti-bacterial-agents, and neutralizing agents (particularly alkaline materials). Such optional additives may be preferably comprised in the composition when the base material is selected from enteric cellulose materials such as hydroxypropyl methyl cellulose acetate succinate (HPMCAS) or hydroxypropyl methyl cellulose phthalate (HPMCP).

The film forming capsule base material may be selected from one or more celluloses (like HPMC, HPMCP, HPMCAS, MC), gelatin, pullulan, and mixtures thereof. Most preferred are celluloses, and particularly hydroxypropyl methylcellulose (HPMC).

The HPMC methoxy and hydroxypropoxy contents herein are expressed according to the USP30-NF25. The viscosity of the HPMC 2% weight solution in water at 20° C. is measured according to the USP30-NF25 method for cellulose derivatives.

Preferably the aqueous composition comprises 17-23% by weight, based on the total weight of the aqueous composition, of the hydroxypropyl methyl cellulose. Suitable hydroxypropyl methyl celluloses are commercially available. For example suitable types are all those fulfilling the requirements set forth in USP30-NF25 for HPMC type 2906.

Suitable aqueous compositions can be obtained by blending HPMCs of same type but different viscosity grade.

In a preferred embodiment, the HPMC in the aqueous composition herein is a HPMC having a viscosity of 4.0 to 5.0 cPs as a 2% w/w solution in water at 20° C.

Viscosity of the HPMC solution in water can be measured by conventional techniques, e.g. as disclosed in the USP by using a viscometer of the Ubbelohde type.

In an embodiment, the aqueous compositions herein may contain between 0% and 5%, preferably between 0% and 2% by weight based on the total weight of the aqueous composition of additional non animal-derived film-forming polymers typically used for the manufacture of hard capsules. In an embodiment, the HPMC aqueous compositions of the invention contain no other film-forming polymer beside the HPMC presently disclosed. Non animal-derived film-forming polymers are for example polyvinyl alcohol, plant-derived or bacterial-derived film-forming polymers. Typical plant-derived film-forming polymers are starch, starch derivatives, cellulose, celluloses derivatives other than the HPMC as defined herein and mixtures thereof. Typical bacterial-derived film-forming polymer are exo-polysaccharides. Typical exo-polysaccharides are xanthan, acetan, gellan, welan, rhamsan, furcelleran, succinoglycan, scleroglycan, schizophyllan, tamarind gum, curdlan, pullulan, dextran and mixtures thereof.

In a preferred embodiment, the HPMC aqueous compositions herein contain between 0% and 1%, preferably 0% by weight based on the total weight of the aqueous composition of animal-derived materials conventionally used for the manufacture of hard capsules. A typical animal-derived material is gelatin.

In a preferred embodiment, the aqueous compositions herein contain less than 0.2%, preferably less than 0.1%, preferably 0% (i.e. in most preferred embodiments the composition herein is free of gelling system) by weight based on the total weight of the aqueous composition of a gelling system. By "gelling systems" it is meant one or more cations and/or one or more gelling agents. Typical cations are $K^+$, $Na^+$, $Li^+$, $NH_4^+$, $Ca^{++}$, $Mg^{++}$ and mixtures thereof. Typical gelling agent(s) are hydrocolloids such as alginates, agar gum, guar gum, locust bean gum (carob), carrageenans, tara gum, gum arabic, ghatti gum, khaya grandifolia gum, tragacanth gum, karaya gum, pectin, arabian (araban), xanthan, gellan gum, konjac mannan, galactomannan, funoran, and mixtures thereof. As usually, gelling agents can optionally be used in combination with cations and other ingredients such as sequestering agents.

As the HPMC aqueous compositions disclosed herein are suitable to give strong and physically stable gels without gelling systems, the dissolution properties of the HPMC capsules of the invention are not affected by the drawbacks typically associated with gelling systems, notably cations.

At the natural state—i.e. without the addition of colorants or similar ingredients in the composition—the HPMC hard capsules obtainable from the aqueous compositions herein show good clarity and transparency. The transmittance measured by UV at 650 nm on the capsule body (through its double shell layers) is around 80%, identical to gelatine hard capsules.

Colorants for use in compositions described herein are natural colorants or coloring foodstuff concentrates. Such colorants are selected such to consist of ones being hydrophilic, since such have been found to be particularly useful in mixing in aqueous hard capsule compositions leading to improved stability of the resulting capsules. An advantage is to additionally not require addition of further materials such as anti-oxidants, preservatives, vitamins and the like for added functionality, and further enables the incorporation of such colorants directly into the aqueous film forming composition without further dilution/dispersion into other media that typically would include surfactants, dispersants and solvents (e.g. organic solvents).

The colorants may be liquid in form or in powder form the latter typically by atomization process or preferably freeze-dried. If in powder there are preferably in freeze-dried powder form, since it has been advantageously found that their dispersion capabilities in aqueous compositions for dip-molded capsules is well retained. Most preferred colorants are however in liquid form.

Generally, 0.01 to 10.0%, preferably 0.1 to 8%, more preferably 1% to 7%, even more preferably 2% to 6%, even more preferably from 3.5% to 5.5%, by weight of colorant can be included in the aqueous composition. The weight is expressed over the total weight of the composition. Optionally, an appropriate plasticizer such as glycerine or propylene glycol can be included in the aqueous solutions. To avoid an excessive softness, the plasticizer content has to be low, such as between 0% and 2%, more preferably between 0% and 1% by weight over the total weight of the composition.

The coloring foodstuff concentrates typically have an enrichment factor (Fe) of less than 6, preferably less than 5.5, more preferably less than 5, even more preferably less than 4.5, most preferably from 1 to 4.4, as measured according to the method described herein. An advantage of this embodiment is to provide a natural colorant that may provide additional functional (in particular aromatic, sapid or nutritive) attributes to the resulting capsule. A further advantage is the addition of such added functionality to the resulting hard capsule shells without adding any further materials during the preparation of the aqueous composition which may negatively alter the resulting stability thereof.

In a preferred embodiment, the composition is free of organic solvents, and is particularly free of at least ethanol or acetone, preferably free of solvents selected from the group consisting of ethanol, acetone, ethyl acetate, butyl acetate, and mixtures thereof.

The source material of the coloring foodstuff concentrates is typically selected from the group consisting of vegetables, preferably selected from purple carrot, pumpkin, yam, radish, sweet potato, beetroot, and mixtures thereof; fruits, preferably selected from elderberry, blackcurrant, grape, apple, huito, and mixtures thereof; comestible plants; algae; fungi preferably selected from safflower, carthamus, hibiscus, tropaeolum, spirulina, chlorella, and mixtures thereof; and mixture thereof. It has been found that such materials result in acceptable physically and light stable colored capsules.

Most preferred source materials are selected from the group consisting of purple carrot, sweet potato, safflower, spirulina, and mixtures thereof. Such provide satisfactory physical and light stability and are found to be very well suited for mixtures for providing different color shades.

Source materials that are less preferred typically include orange, curcuma, tomato and carrot (or other carotene dispersions). Such typically have been found to have innate characteristics of the food product which make them less suitable for the particular use in hard capsule manufacture, particularly due to pH sensitivity as well as poor light stability over time.

Colorants not suitable, and thus presently generally excluded by the disclosure, include the following non-limiting list of materials: R3 (erythrosine B), R3 opaque (erythrosine B), Y6 (sunset yellow), Y6 opaque (sunset yellow), B2 (indigotine), B2 opaque (indigotine), Y5 (tartrazine), Y5 opaque (tartrazine), R40 (allura red), R40 opaque (allura red), Y10 (quinolein), Y10 opaque (quinolein), synthetic tar pigment, iron oxide, titanium dioxide or carbon black, carotenoid-based pigments, annatto dye (for example, bixin, norbixin), gardenia yellow pigment (for example crocin), extracted carrot pigment (for example β-carotene), extracted orange pigment (for example β-apo-β-carotenal), extracted paprika pigment (For example capsanthin), extracted mushroom pigment (eg canthaxanthin), extracted tomato pigment (for example, lycopene), and the like, extracted purple sweet potato pigment anthocyanin systems, extracted grape skin pigment (for example Enoshianin), extracted perilla pigment (for example shisonin), extracted red cabbage pigment (for example Le Bro brush true), extracted chalcone of the safflower yellow pigment, extracted buckwheat pigment (for example rutin), extracted black oak skin pigment (eg quercetin), extracted sorghum pigment (for example apigenin), extracted cacao pigment, laccaic acid, carmine acid, alizarin, and the like, powdered/extracted catechutannic acid, extracted turmeric, methylrosanilinium chloride, yellow iron oxide, yellow iron sesquioxide, orange essence, brown iron oxide, carbon black, carmine, carotene liquid, β-carotene, light sensitive element No. 201, gold leaf, sasa albomarginata extract, black iron oxide, light anhydrous silicic acid, zinc oxide, titanium oxide, iron sesquioxide, disazo yellow, food blue No. 1 and its aluminum lake, food blue No. 2 and its aluminum lake, food Yellow No. 4 and its aluminum lake, food Yellow No. 5 and its aluminum lake, food Green No. 3 and its aluminum lake, food red No. 2 and the aluminum lake, food red No. 3, food red No. 102 and its aluminum lake, food red No. 104 and its aluminum lake, food red No. 105 and its aluminum lake, food Red No 106 and its aluminum lake, sodium hydroxide, talc, copper chlorophyll sodium, copper chlorophyll, rye green leaf extract, phenol red, sodium fluorescein, d-borneol, malachite green, octyl dodecyl myristate, methylene blue, medicinal carbon, riboflavin butyrate, riboflavin, manganese ammonium phosphate, riboflavin sodium phosphate, rose oil, turmeric color, chlorophyll, carminic acid color, food red No. 40 and its aluminum lake, sodium iron-chlorophyllin, dunaliella carotene, paprika colour, ginseng carotene, potassium norbixin, sodium norbixin, palm oil carotene, extracted beet red, extracted grape pericarp color, extracted black currant color, extracted monascus color, extracted safflower red color, extracted marigold color, sodium riboflavine phosphate, madder color, alkanet color, aluminum, potato carotene, extracted shrimp color, extracted krill color, extracted orange color, extracted cacao color, extracted cacao carbon-dust color, extracted oyster color, extracted crab color, extracted carob color, extracted fish scale foil, silver, extracted kusagi color, extracted gardenia blue color, extracted gardenia red color, extracted gardenia yellow color and kooroo color, chlorophine, extracted kaoliang color, extracted bone char color, extracted bamboo grass color, extracted shea nut color, extracted lithosperm root color, extracted redsanders color, vegetable carbon black, extracted sappan color, extracted onion color, extracted tamarind color, extracted corn color, extracted tomato color, extracted peanut color, extracted phaffia color, pecan nut color, extracted monascus yellow, extracted hematococcus algae color, extracted purple sweet potato pigment, extracted purple corn color, extracted purple yam color, vegetable oil soot color, lac color, rutin, enju extract, backwheat extract, logwood color, extracted red cabbage color, extracted red rice color, extracted azuki color, extracted hydrangeae leaves extract, uguisukagura color, extracted elderberry color, extracted olive tea color, extracted cowberry color, extracted gooseberry color, extracted cranberry color, extracted salmon berry color, extracted strawberry color, extracted dark sweet cherry color, extracted cherry color, extracted thimbleberry color, extracted deberry color, extracted pineapple color, extracted huckleberry color, extracted grape juice color, extracted black currant color, extracted blackberry color, extracted plum color, extracted blueberry color, extracted berry color, extracted boysenberry color, extracted whortleberry color, extracted mulberry color, extracted morello cherry color, extracted raspberry color, extracted red currant color, extracted lemon juice color, extracted loganberry color, extracted cocoa color, extracted saffron color, extracted beefsteak plant color, extracted chicory color, extracted layer color, extracted hibiscus color, malt extract, extracted powdered paprika, extracted beet red color, extracted ginseng color, and the like.

Colorants that are generally particularly excluded by the disclosure include lipophilic beta-carotene pigments, hydrophilic flavonoids, chlorophyll and/or phycocyanin pigments. Indeed such are examples of extracted pigments. Moreover, carotenoids are generally lipophilic, requiring thus additional species such as dispersing gents or surfactants, to be able to incorporate them into water-based compositions.

The compositions described herein may further comprise opacifiers (like titanium oxide), however, if present, such are in amounts of less than 1.5%, preferably less than 0.5%, more preferably less than 0.2%, even more preferably less than 0.1%, and more preferably 0% (i.e. free of opacifiers), by weight of the composition.

It has been noted that the aqueous compositions herein allow the manufacture of good, particularly HPMC, hard capsules showing optimal dissolution properties. Dissolution profile is a key point in therapy to obtain a complete and reproducible release of the substance contained in the capsule.

Additionally, it has been noted that the aqueous compositions herein allow the manufacture of good hard capsules whose bodies and caps, once telescopically joined, can suitably be sealed. This makes the presently disclosed new hard capsules a particularly good and cost-effective solution for the manufacture of liquid-filled oral dosage forms as well as powder-filled dosage forms for inhalation or the manufacture of tamper-proof pharmaceutical forms to be used in the context of double-blind trials.

The Dosage Form Article

Dosage form articles herein are in the form of hard capsules that provide at least one compartment for filling a medicament therein. Such hard capsules comprise at least two shells (forming a two-piece hard capsule) typically comprising a body part and a cap part telescopically fitted thereover.

In a preferred embodiment, the capsule shells are obtainable by the aqueous composition and/or process disclosed herein.

The hard capsules herein comprise a film forming capsule base material and one or more colorants each colorant consisting of a hydrophilic coloring foodstuff concentrate described herein above.

In a preferred embodiment, the capsule has a color stability, $\Delta E_{2000}$, after 5 weeks under constant illumination (as described in the test method herein) storage at room temperature, of less than 16, preferably less than 15, more preferably less than 12, even more preferably from 1 to 11, most preferably from 2 to 10. Advantageously, it has been found that capsules meeting such parameter show good light stability and minimal fading with time under in use production, storage and ultimate use conditions.

In a preferred embodiment, the capsule shell contains HPMC in an amount between 70 and 99%, preferably between 80 and 99% by weight based on the shell weight. If no other film-forming polymers are present, the HPMC is preferably between 92% and 99%, more preferably between 93 and 98%, even more preferably between 94% and 97% by weight based on the shell weight. In a preferred embodiment, the capsule shell contains between 0% and 25%, preferably between 0% and 10% by weight based on the shell weight of additional non animal-derived film-forming polymers as defined above.

In a preferred embodiment, the capsule shell contains water between 1 to 8%, preferably between 2 and 7%, more preferably between 3 and 6% by weight based on the empty shell weight (measured at room temperature and pressure and relative humidity RH of about 50%).

In a preferred embodiment, the colorants discussed above are comprised in the capsule in a total amount of, between 0 and 10%, preferably between 0.001 and 5%, more preferably between 0.01 and 3%, by weight based on the empty shell weight.

In an embodiment, the capsule shell contains one or more plasticizers in a total amount of, between 0 and 10%, preferably between 0.001 and 5%, more preferably between 0.01 and 3%, by weight based on the empty shell weight.

In an embodiment, the capsule shell contains one or more antibacterial agents between 0 and 2%, preferably between 0.001 and 1%, more preferably between 0.01 and 0.5%, by weight based on the shell weight.

In an embodiment, the capsule shell contains one or more flavourings agents between 0 and 2%, preferably between 0.001 and 1%, more preferably between 0.01 and 0.5%, by weight based on the shell weight.

In a preferred embodiment, the hard capsule shell presently disclosed can be used for the manufacture of tamper-proof pharmaceutical dosage forms. To this end, it is particularly advantageous if the capsule shell is as disclosed in EP 110500 B1. In this preferred embodiment, the, preferably HPMC, hard capsule shell comprises coaxial cap and body each of the cap and body having a generally cylindrical side wall, an open end and a closed end region, the side wall of each of said parts is substantially greater than the capsule shell diameter, the cap and body being adapted to be joined in telescopic relationship wherein, when the cap and body are fully joined in telescopic relationship, the only portion of the body which is exposed is the closed end region, and wherein the closed end region has an outer surface which is of such a configuration as to resist being gripped, whereby separation of the cap and body is impeded, and wherein when the cap and body are fully joined in telescopic relationship, the inner side wall of the cap is substantially totally overlapped by the outer side wall of the body. In other words, when the cap and body are fully joined in telescopic relationship, the side wall of the cap encases the entire side wall of the body. Thus, in use, only the body closed end is exposed and presents a minimal surface for gripping and withdrawal of the body from within the cap, thereby impeding separation of the capsule shell.

The closed end region of either the body and the cap may, for example, have a configuration which is generally hemi-spheroidal, pyramidal, conical or flat.

For additional security, it is preferred that the body and the cap further include mutual locking means comprising one or more circumferentially extending ridges and/or grooves. Thus, the capsule shell may be such that the side wall of one of the cap and body has a locking means comprising one or more circumferentially extending ridge extending either (i) radially inwardly from an inner surface of the side wall of the cap or (ii) radially outwardly from an outer surface of the side wall of the body, as the case may be.

Alternatively, or in addition, the side wall of the other of the cap and body has one or more circumferentially extending groove extending either (i) radially inwardly from the outer surface of the body or (ii) radially outwardly from the inner surface of the cap, as the case may be, and engaging a respective ridge.

It is preferred that the capsule shell further includes venting means to permit air to escape from within the capsule when joined, wherein the or each circumferentially extending ridge comprises two or more segments so that spaces between the segments act as vents to permit air to escape from within the capsule when the cap and body are being joined.

It is preferred that the side wall of one of the cap and body has a pair of diametrically opposed integral indents extending either (i) radially inwardly from the inner surface of the side wall of the cap or (ii) radially outwardly from the outer surface of the side wall of the body, as the case may be; and the diametric spacing of the indents is, in the case (i), less than the outside diameter of the open end of the body or, in the case (ii), greater than the inside diameter of the open end of the cap, such that the body can enter the cap and permit air to escape from within the capsule when the cap and body are being joined.

For storage and/or transportation purposes, it is preferred that the capsule shell may also include means for pre-locking the partially joined caps and bodies in a constant predetermined relative position prior to filling and final joining.

Preferably, bodies have a reduced diameter in the area of their open end in order to avoid abutment when they are telescopically housed within caps.

Alternatively, or in addition, caps have a reduced diameter in the area of their open end, thereby resulting in improved engagement between them and the region of the side wall of the bodies adjacent the closed end region of the bodies, as further resistance to tampering.

In an aspect, the present disclosure relates to a hard capsule defined above comprising a capsule shell as defined above and one or more medicaments filled therein.

When used as dosage form for drugs, capsules of the invention typically comprise for example from 0.001 g to 2.0 g of active ingredient, optionally mixed with one or more pharmaceutically acceptable excipients.

In one embodiment, the, preferably HPMC, hard capsule presently disclosed, optionally sealed, can be used in the context of dry powder inhalers (also commonly know by the acronym DPIs).

Medicament

Drugs (i.e. medicaments) suitable for use in the dosage form articles described herein may take any form and be for any treatment of a human or animal subject. This includes not only pharmaceutical compounds but also dietary supplements such as vitamins, minerals and the like.

The drug may be in a state selected from solid or liquid, preferably solid, at room temperature and atmospheric pressure, and comprises one or more active compounds.

Suitable compounds (and generally encompassed by the term "medicament" as used herein) for delivery according to the disclosure include, but are not limited to, particulate, powder, waxy, liquid, and/or pellet forms of the following:
a) pharmaceuticals (also called pharmaceutical actives) such as betamethasone, thioctic acid, sotalol, salbutamol, norfenefrine, silymahn, dihydroergotamine, buflomedil, etofibrate, indomethacin, oxazepam, acetyldigitoxins, piroxicam, halopehdol, isosorbide mononitrate, amithptyline, diclofenac, nifedipine, verapamil, pyritinol, nitrendipine, doxy-cycline, bromhexine, methylprednisolone, clonidine, fenofibrate, allopurinol, pirenzepine, levothyroxine, tamoxifen, metildigoxin, o-(B-hydroxyethyl)-rutoside, propicillin, aciclovirmononitrate, paracetamolol, naftidrofuryl, pentoxifylline, propafenone, acebutolol, 1-thyroxin, tramadol, bromocriptine, loperamide, ketofinen, fenoterol, cadobesilate, propranolol, minocycline, nicergoline, ambroxol, metoprolol, B-sitosterin, enalaprilhydrogenmaleate, bezafibrate, isosorbide dinitrate, gallopamil, xantinolnicotinate, digitoxin, flunitrazepam, bencyclane, depanthenol, pindolol, lorazepam, diltiazem, piracetam, phenoxymethylpenicillin, furosemide, bromazepam, flunarizine, erythromycin, metoclopramide, acemetacin, ranitidine, biperiden, metamizol, doxepin, dipotassiumchloraze-pat, tetrazepam, estramustinephosphate, terbutaline, captopril, maprotiline, prazosin, atenolol, glibenclamid, cefaclor, etilefrin, cimetidine, theophylline, hydromorphone, ibu-profen, primidone, clobazam, oxaceprol, medroxyprogesterone, flecainide, Mg-pyhdoxal-5-phosphateglutaminate, hymechromone, etofyllineclofibrate, vincamine, cin-narizine, diazepam, ketoprofen, flupentixol, molsidomine, glibornuhde, dimethindene, melperone, soquinolol, dihydrocodeine, clomethiazole, clemastine, glisoxepid, kallidino-genase, oxyfedhne, baclofen, carboxymethylcystsin, thioredoxin, betahistine, 1-tryptophan, myrtol, bromelain, prenylamine, salazosulfapyridine, astemizole, sulpiride, benzerazid, dibenzepin, acetylsalicylic acid, miconazole, nystatin, ketoconazole, sodium picosulfate, colestyramate, gemfibrozil, rifampin, fluocortolone, mexiletine, amoxicillin, terfenadine, mucopolysaccharidpolysulfuric acid, triazolam, mianserin, tiaprofensaure, ameziniummethylsulfate, mefloquine, probucol, quinidine, carbamazepine, Mg-1-aspartate, penbutolol, piretanide, amitriptyline, caproteron, sodium valproinate, me-beverine, bisacodyl, 5-amino-salicyclic acid, dihydralazine, magaldrate, phenprocou-mon, amantadine, naproxen, carteolol, famotidine, methyldopa, auranofine, estriol, nadolol, levomepromazine, doxorubicin, medofenoxat, azathioprine, flutamide, norfloxacin, fendiline, prajmaliumbitartrate, aescin acromycin, anipamil, benzocaine, [beta]-carotene, cloramphenicol, chlorodiazepoxid, chlormadinoneacetate, chlorothiazide, cin-narizine, clonazepam, codeine, dexamethasone, dicumarol, digoxin, drotaverine, grami-cidine, griseofulvin, hexobarbital hydrochlorothiazide, hydrocortisone, hydroflumethiazide, ketoprofen, lonetil, medazepam, mefruside, methandrostenolone, sulfaperine, nalidixic acid, nitrazepam, nitrofurantoin, estradiol, papaverine, phenacetin, phenobarbi-tal, phenylbutazone, phenytoin, prednisone, reserpine, spironolactine, streptomycin, sul-famethizole, sulfamethazine, sulfamethoxoazole, sulfamethoxydiazinon, sulfathiazole, sulfisoxazole, testosterone, tolazamide, tolbutamide, trimethoprim, tyrothricin, antacids, reflux suppressants, antiflatulents, antidopaminergics, proton pump inhibitors, H2-receptor antagonists, cytoprotectants, prostaglandin analogues, laxatives, antispasmodics, antidiarrhoeals, bile acid sequestrants, opioids, beta-receptor blockers, calcium channel blockers, diuretics, cardiac glycosides, antiarrhythmics, nitrates, antianginals, vasoconstrictors, vasodilators, ACE inhibitors, angiotensin receptor blockers, alpha blockers, anticoagulants, heparin, antiplatelet drugs, fibrinolytic, anti-hemophilic factor, haemostatic drugs, hypolipidaemic agents, statins, hypnotics, anaesthetics, antipsychotics, antidepressants (including tricyclic antidepressants, monoamine oxidase inhibitors, lithium salts, selective serotonin reuptake inhibitors), antiemetics, anticonvulsants, an-tiepileptics, anxiolytics, barbiturates, movement disorder drugs, stimulants (including amphetamines), benzodiazepine, cyclopyrrolone, dopamine antagonists, antihistamines, cholinergics, anticholinergics, emetics, cannabinoids, 5-HT antagonists, analgesics, muscle relaxants, antibiotics, sulfa drugs, aminoglycosides, fluoroquinolones, bronchodilators, NSAIDs, anti-allergy drugs, antitussives, mucolytics, decongestants, corticosteroids, beta-receptor antagonists, anticholinergics, steroids, androgens, antian-drogens, gonadotropin, corticosteroids, growth hormones, insulin, antidiabetic drugs (including sulfonylurea, biguanide/metformin, and thiazolidinedione), thyroid hormones, antithyroid drugs, calcitonin, diphosponate, vasopressin analogs, contraceptives, follicle stimulating hormone, luteinising hormone, gonadotropin release inhibitor, progestogen, dopamine agonists, oestrogen, prostaglandin, gonadorelin, clomiphene, tamoxifen, di-ethylsti 1 bestrol, antimalarials, anthelmintics, amoebicides, antivirals, antiprotozoals, vaccines, immunoglobulin, immunosuppressants, interferon, monoclonal antibodies, and mixtures thereof;

b) vitamins, e.g., fat-soluble vitamins such as vitamins A, D, E, and K, and water soluble vitamins such as vitamin C, biotin, folate, niacin, pantothenic acid, riboflavin, thiamin, vitamin B6, vitamin B12, and mixtures thereof;

c) minerals, such as calcium, chromium, copper, fluoride, iodine, iron, magnesium, manganese, molybdenum, phosphorus, potassium, selenium, sodium (including sodium chloride), zinc, and mixtures thereof;

d) dietary supplements such as herbs or other botanicals, amino acids, and substances such as enzymes, organ tissues, glandulars, and metabolites, as well as concentrates, metabolites, constituents, extracts of dietary ingredients, oils such as krill oil and mixtures thereof;

e) homoeopathic ingredients such as those listed in the Homeopathic Pharmacopoeia of the United States Revision Service (HPRS), and mixtures thereof. It must be recognized, of course, that the HPRS is periodically updated and that the present invention includes homeopathic ingredients that may be added to the HPRS;

f) probiotics and yeast, such as bacteria selected from the group consisting of *Lactobacillus* (Döderlein's bacilli) such as *Lactobacillus crispatus, Lactobacillus jensinii, Lactobacillus johnsonii, Lactobacillus gasseri, Enterococcus faecium*, or fungi selected from the group of *Saccharomycetales* such as *Saccharomyces boulardii*.

g) hormones, such as estrogen (i.e. a natural estrogen or a synthetic compound that mimics the physiological effect of natural estrogens) including, without limitation, estradiol (17-estradiol), estridiol acetate, estradiol benzoate, estridiol cypionate, estridiol decanoate, estradiol diacetate, estradiol heptanoate, estradiol valerate, 17a-estradiol, estriol, estriol succinate, estrone, estrone acetate, estrone sulfate, estropipate (piperazine estrone sulfate), ethynylestradiol (17a-ethynylestradiol, ethinylestradiol, ethinyl estradiol, ethynyl estradiol), ethynylestradiol 3-acetate, ethynylestradiol 3-benzoate, mestranol, quinestrol, nitrated estrogen derivatives or combinations thereof; or progestin (i.e. natural or synthetic compounds that possesses progestational activity including, without limitation, nortestosterone, ethynyltestosterone, deacetylnorgestimate, hydroxyprogesterone, 19-norprogesterone, 3P-hydroxydesogestrel, 3-ketodesogestrel (etonogestrel), acetoxypregnenolone, algestone acetophenide, allylestrenol, amgestone, anagestone acetate, chlormadinone, chlormadinone acetate, cyproterone, cyproterone acetate, demegestone, desogestrel, dienogest, dihydrogesterone, dimethisterone, drospirenone, dydrogesterone, ethisterone (pregneninolone, 17a-ethynyltestosterone), ethynodiol diacetate, fluorogestone acetate, gastrinone, gestadene, gestodene, gestonorone, gestrinone, hydroxymethylprogesterone, hydroxymethylprogesterone acetate, hydroxyprogesterone, hydroxyprogesterone acetate, hydroxyprogesterone caproate, levonorgestrel (1-norgestrol), lynestrenol (lynoestrenol), mecirogestone, medrogestone, medroxyprogesterone, medroxyprogesterone acetate, megestrol, megestrol acetate, melengestrol, melengestrol acetate, nestorone, nomegestrol, norelgestromin, norethindrone (norethisterone) (19-nor-17a-ethynyltestosterone), norethindrone acetate (norethisterone acetate), norethynodrel, norgestimate, norgestrel (d-norgestrel and dl-norgestrel), norgestrienone, normethisterone, progesterone, promegestone, quingestanol, tanaproget, tibolone, trimegestone, or combinations thereof. And mixtures in any combination of the foregoing.

The Processes and Uses

The aqueous compositions described herein are typically used as dipping compositions in dip-molding processes for the manufacture of hard capsules.

Dip-molding processes for making two-piece hard capsules herein comprise the steps of: providing an aqueous composition comprising a film forming capsule base material;

directly mixing one or more colorants each consisting of hydrophilic coloring foodstuff concentrates with said aqueous composition to provide a dipping composition;

dipping one or more mold pins in said dipping composition;

extracting said one or more mold pins from said dipping composition such that a film is formed over said pins; and drying said films to provide capsule shells.

The most preferred film forming capsule base material comprises, preferably consists of, one or more celluloses such as hydroxypropyl methylcellulose (HPMC). Such has the advantage of enabling a lower composition temperature during the dipping thermogelation process (cold gelation process) which limits the color degradation and/or instability of the selected coloring foodstuff concentrates. Thus the "cold gelation" (thermogelation) process with HPMC, where the dip composition is kept at a temperature below gelation and rather the mold pins are heated at temperatures above gelation prior immersion therein, is particularly preferred and selected for generating physically stable hard capsules comprising natural colorants (or hydrophilic coloring foodstuff concentrate) described herein. Such has the further advantage of resulting in fully vegetarian dosage forms with better patience acceptance by some particular groups of subjects (e.g. having dietary or religious requirements) whilst for example allowing higher levels of such colorants to be incorporated for effectively providing further functional attributes to the capsules as described herein.

In a preferred embodiment, the aqueous composition is kept at a temperature of from 25° C. to 45° C., preferably from 30° C. to 40° C. Typically, in such embodiments film forming is achieved by cold gelation and the pins are as such pre-heated to a temperature that is greater than the gelation temperature of the composition prior to the dipping step.

In a preferred embodiment, the aqueous composition and the dipping composition have a pH of less than 6, preferably less than 5, more preferably from 3 to 4.9, even more preferably from 3.5 to 4.8, most preferably from 4.0 to 4.7. Such pH range has been found particularly beneficial to avoid degradation of the particular natural colorants described above and as such improve stability of the composition and resulting capsules.

The drying step is preferably carried out at a temperature of less than 65° C., preferably less than 60° C., even more preferably from 40° C. to 55° C. Advantageously such temperatures still enable effective drying of the hard capsules without degradation of the natural colorants.

In an embodiment, the aqueous compositions herein can be prepared by dispersing the capsule base film forming material (e.g. HPMC) and the other optional ingredients in water. The aqueous solvent can be at a temperature above room temperature, preferably below 60° C., more preferably below 50° C. In a preferred embodiment after de-bubbling, the dispersion is cooled down below room temperature, preferably below 15° C., to achieve the solubilisation of the cellulose (e.g HPMC).

The gelling temperature of the aqueous compositions may be determined by a measurement of the viscosity by progressively heating the composition. The temperature at which the viscosity starts to sharply increase is considered as the gelling temperature. As an example, for a concentration of about 19% w/w in water, any HPMC of the invention fulfilling the USP definition of HPMC type 2906 has a gelling temperature of about between 30 and 40° C. As an additional example, for concentrations between 15 and 25% w/w in water, an HPMC of the invention fulfilling the USP definition of HPMC with a hydroxypropoxy content of about 6%, has a gelling temperature between about 30 and 40° C.

In an aspect, the present disclosure relates to a process for the manufacture of hydroxypropyl methyl cellulose hard capsules according to a dip coating process, characterized in that it comprises the steps of: (a) providing an aqueous composition of a hydroxypropyl methyl cellulose having a methoxy content of 27.0-30.0% (w/w), a hydroxypropoxy content of 4.0-7.5% (w/w) and a viscosity of 3.5-6.0 cPs as a 2% weight solution in water at 20° C., wherein the concentration of the hydroxypropyl methyl cellulose in the aqueous composition is chosen to obtain a viscosity of the aqueous composition of 1000 to 3000 cPs, preferably 1200 to 2500 cPs, more preferably 1600 to 2000 cPs, measured at a temperature of 10° C. to 1.0<0>C below the aqueous composition gelling temperature; (b) mixing the aqueous composition with one or more colorants each consisting of hydrophilic coloring foodstuff concentrates; (c) pre-heating dipping pins so that they are at 55-95° C. when dipped into the aqueous composition; (d) dipping the pre-heated dipping pins into the aqueous composition maintained at a temperature of 1° C. to 10° C. below its gelling temperature; (e) withdrawing the dipping pins from the aqueous composition obtaining a film on the dipping pins and (f) drying the film on the dipping pins at a temperature above the gelling temperature of the aqueous composition so as to obtain molded capsule shells on the pins. Steps (a) and (b) and (d) to (f) are typically to be performed in the order they are presented.

In step (a) the aqueous compositions of the invention can be used. An optional adjustment of the HPMC concentration can be performed to meet the viscosity ranges indicated above.

In step (c), the temperature range of pre-heated pins is 55-95° C. meaning that this is the pin temperature when pins are dipped. Preferably the temperature is 60-90° C., more preferably 60-85° C., more preferably 65-85° C., even more preferably 70-80° C. It is preferred that such temperature be chosen according to the desired capsule size. By "according to the capsule size" it is meant that the smaller the pin dimension, the higher the temperature. For example, for an HPMC type 2906 (USP classification) and within the HPMC weight ranges defined above for the aqueous composition, for a capsule size 00 (conventionally considered a large capsule size), the pin temperature is preferably between 70 and 80, for a capsule size 1 (conventionally considered a medium capsule size), the pin temperature is preferably between 80 and 90, and for a capsule size 4 (conventionally considered a small capsule size), the pin temperature is preferably between 85 and 95.

In step (d), the dipping composition is maintained at a temperature of 10° C. to 1.0° C., preferably 6° C. to 2.0° C., below its gelling temperature. For example, if a dipping composition has a gelling temperature of about 36.0° C., it can be maintained at a temperature of for example about 34.0° C.

After being withdrawn from the dipping composition, the pins can be turned from a "top-down" dipping position to a "top-up" drying position according to conventional capsule molding processes. In this step the pins are rotated about a horizontal axis of about 180° with respect to the dipping position of step (d).

By drying in step (f) the object is to reduce the water content in the capsule shells on the pins. Generally, the water content in the molded capsule shells is reduced from around 80% to around 7% by weight, based on the total weight of the molded capsule shells. Step (f) is typically carried out for a period of time of from 30 to 60 minutes, preferably not exceeding the above identified temperatures.

Normally, caps and bodies have a side wall, an open end and a closed end. The length of the side wall of each of said parts is generally greater than the capsule diameter. Thus, the hard capsules of the present disclosure do not structurally depart from the conventional definition of hard capsules. "Capsule" refers to both empty and filled capsules.

The molded capsule shells mentioned to above, generally refer to both bodies and caps, depending on the shape of the mold pin. Thus, after step (e) the dried capsule shells on the dipping pins can be processed according to conventional steps. This means that in general after step (e), the capsule shells (bodies and caps) are stripped from the pins. This step can be followed by cutting the stripped shells to a desired length.

Typically, hard capsule dip-molding manufacturing processes encompass an additional step of lubricating the pins so as to make it easier to strip the capsule shells from the pins. Lubrication is normally achieved via the application of a demolding agent to the pins surface.

Once filled, the capsules can be made tamper-proof by using any solution conventionally used in the field of hard capsules to make the joint permanent. Banding or sealing are suitable techniques. Sealing is a technique well known in the field of hard shell capsules. Various alternative techniques are currently used for this purpose. A suitable procedure is disclosed for example in U.S. Pat. Nos. 4,539,060 and 4,656,066. Many improvements of sealing procedure are currently available.

According to a know sealing process, the capsule is (i) contacted with a sealing fluid, (ii) excess sealing fluid is removed from the surface and (iii) the capsule is dried so as to induce curing and make the seal permanent.

For example alcohol/water mixtures can be used as sealing fluids, such as ethanol/water mixtures. The good sealing quality obtained makes the sealed capsule of the disclosure particularly suitable for the manufacture of leakage-free dosage forms particularly for use in the administration of substances in liquid form. By "sealing quality" it is meant either the visual quality and/or the adhesion strength of the sealing.

The above aqueous compositions and process are particularly suitable for manufacturing HPMC hard capsules that dissolve at a rate comparable to conventional gelatine capsules. Such capsules can be manufactured at an industrial scale with process speeds comparable to gelatine capsules. Their mechanical properties are better than those of conventional gelatine capsules since they are less brittle, particularly under extremely dry atmosphere. Their visual appearance is similar to that of gelatine capsules.

A preferred aspect of the disclosure consists of the use of one or more colorants, each said colorant consisting of a hydrophilic coloring foodstuff concentrate (generally as described above), in hard capsules, typically to provide a color and a functional attribute to said capsule, said functional attribute being selected from the group consisting of aromatic, sapid or nutritive properties. Such hydrophilic coloring foodstuff concentrate preferably selected from concentrates of carrot, purple carrot, pumpkin, yam, radish, sweet potato, beetroot, elderberry, blackcurrant, grape, apple, huito, safflower, carthamus, hibiscus, tropaeolum, spirulina, chlorella, and mixtures thereof, preferably purple carrot, sweet potato, safflower, spirulina, and mixtures thereof.

The scope of the invention can be understood better by referring to the examples given below, the aim of which is to explain the advantages of the invention. Unless otherwise specified, all parts and percentages are by weight. Composition viscosities were determined by Brookfield viscometer.

Test Methods

Color Stability

Color stability is carried out in an accelerated constraining test condition via a light-climate test cabinet with temperature regulation and 2 light sources comprising a cool white fluorescent lamp and a near UV fluorescent lamp and following the procedure outlined in: *ICH harmonised tripartite guideline, stability testing: photostability testing of new drug substances and products Q1B*, 6 Nov. 1996 (the whole contents of which is herein included by reference). The test is set to reach 1.2 Mio Lux·hours threshold (e.g. after a 5 week intense/accelerated exposure/storage with an Incubator BCR 240 from Firlabo).

A. Light Source

The light sources described below is used for photostability testing. The temperature is controlled to minimize the effect of localized temperature changes and a dark control is included in the same environment.

The same sample is exposed to both the cool white fluorescent and near ultraviolet lamp. 1. A cool white fluorescent lamp designed to produce an output similar to that specified in ISO 10977(1993); and 2. A near UV fluorescent lamp having a spectral distribution from 320 nm to 400 nm with a maximum energy emission between 350 nm and 370 nm; a significant proportion of UV should be in both bands of 320 to 360 nm and 360 to 400 nm.

B. Procedure

Samples are exposed to light providing an overall illumination of about 1.2 million lux hours and an integrated near ultraviolet energy of about 200 watt hours/square meter.

Samples are exposed side-by-side with a validated chemical actinometric system to ensure the specified light exposure is obtained, or for the appropriate duration of time when conditions have been monitored using calibrated radiometers/lux meters.

For the dark control, samples are wrapped in aluminum foil and placed alongside the rest of the samples.

HPMC capsules are made according to the dip-molding process herein described comprising a number of different coloring agents to generate samples for the color stability test. The formulation of Example 1 is repeated for the different coloring materials to generate samples of each capsule type (n=5). The only variable being the change of coloring substance. At least one sample for each colored capsule is placed under the light condition test described above and one identical control sample is placed in dark conditions according to the above procedure (for an equivalent time period of 5 weeks).

C. $\Delta E_{2000}$ Measurement

For each of the samples the $\Delta E_{2000}$ (also referred to as CIEDE2000) is measured following ISO norm n° ISO/CIE 11664-6:2014 (CIE S 014-6/E:2013) with Color Eye XTH spectrocolorimeter from GretagMacBeth, associated with software Color iQC. Sphere instrument (Standard calibration with green, white and black tiles, illuminant D65-10, color equations according to DE2000).

The results are shown in Tables 1 and 2.

TABLE 1

| Colorant name | % wt coloring product* | supplier | Source | $\Delta E_{2000}$ (light) 5 weeks | $\Delta E_{2000}$ (dark) 5 weeks |
|---|---|---|---|---|---|
| Blue | 1 | WILD | huito | 16.85 | 0.63 |
| Yam | 1 | Kalsec | Yam | 9.64 | 0.27 |
| vivid red | 1 | Kalsec | beetroot | 7.64 | 3.43 |
| turmeric | 1 | Kalsec | curcuma | 18.59 | 0.46 |
| fruit max akaï | 1 | Hansen | spirulina | 13.03 | 0.56 |
| fruit max vanilla | 1 | Hansen | carrot | 21.28 | 2.36 |
| Vegex Lutéin | 1 | Hansen | marigold flower (lutein) | 24.44 | 0.30 |
| vegetone rich red | 1 | Hansen | tomato (lycopene) | 31.15 | 32.33 |
| starfruit bright WS (carthame) | 1 | Hansen | carthame/ safflower | 6.62 | 0.16 |
| Turmeric T PT8 WS | 1 | Hansen | curcuma | 22.96 | 0.07 |
| color fruit yellow 350 WSS | 1 | Hansen | algae carotenoid | N/A** | N/A** |

TABLE 1-continued

| Colorant name | % wt coloring product* | supplier | Source | ΔE$_{2000}$ (light) 5 weeks | ΔE$_{2000}$ (dark) 5 weeks |
|---|---|---|---|---|---|
| pink opaque | 1 | GNT | sweet potato | 7.44 | 0.20 |
| shade blueberry red opaque | 1 | GNT | blackcurrant | 11.56 | 1.19 |
| Shade fruity red clear opaque | 1 | GNT | grape | 10.20 | 1.07 |
| shade Mint green | 1 | GNT | green (mix of spirulina and safflower @ 50:50 wt) | 12.83 | 0.60 |

*For all above tests a 1% wt of specified colorant was added to the composition of Example 1, by weight of the total composition (all other components kept equal).
**non-homogenous composition resulted with unacceptable visual appearance.

TABLE 2

| Colorant name | % wt coloring product* | supplier | source | ΔE$_{2000}$ (light) 5 weeks | ΔE$_{2000}$ (dark) 5 weeks |
|---|---|---|---|---|---|
| Lemon Yellow transparent | 2 | GNT | Carthame/ safflower | 6.19 | 0.30 |
| Summer red transparent | 2 | GNT | radish/ carrot | 5.06 | 0.23 |
| cherry red | 2 | GNT | purple carrot | 6.20 | 1.08 |
| yam | 2 | Kalsec | yam | 14.13 | 0.59 |
| pink | 2 | GNT | sweet potato | 6.36 | 0.28 |
| vivid red | 2 | Kalsec | beetroot | 7.98 | 3.63 |
| shade blue | 2 | GNT | spirulina | 14.44 | 0.53 |
| Shade fruity red clear | 2 | GNT | grape | 9.97 | 1.29 |

*For all above tests a 2% wt of specified colorant was added to the composition of Example 1, by weight of the total composition (all other components kept equal).

As can be observed in the above table coloring concentrates from the following sources are found to be unacceptable for hard capsules as described herein: curcuma, carrot, lutein, tomato, curcuma, and algae carotenoid. In particular, algae carotenoid concentrates exhibit homogeneity issues.

Enrichment Factor Concentration

The enrichment factor as used herein is calculated by first analyzing the coloring substance (or colorant/concentrate) to identify the total % wt of each of carbohydrates, fibres, proteins, lipids and pigment, by weight of the total coloring substance; and repeating the same for the source material used for obtaining the coloring substance.

For example; measuring the amount of proteins by common methods in the art like the Kjeldahl method, generally based on food "digestion" with a strong acid (sulphuric acid), releasing nitrogen, that is then titrated [acc. to § 64 LFGB, Kjeldahl (N×6.25)]; measuring lipids by common methods in the art [acc. to § 64 LFGB, Weilbull-Stoldt, and for saturates DGF C VI 10a, 11d mod.; GC/FID] like NMR spectroscopy; measuring carbohydrates by common methods in the art [IC, HPLC] like alcoholic extraction (e.g. sample is dried, ground, defatted by solvent extraction, then the residue is boiled with an alcoholic solution (e.g. ethanol, methanol, and mixtures) and filtrated. The filtrate is clarified by treatment with an ion-exchange resin, and then finally mono and oligo-saccharides are identified and quantified by chromatography (HPLC); and measuring fibers by common methods in the art like gravimetric [acc. to § 64 LFGB, enzymat.-gravimetric SOP M 1010 nach ASU L 00.00-18].

The below formula (Equation 1) is then used to calculate the enrichment factor.

$$Fe = \frac{Cp \div Np}{Cs \div Ns} \quad \text{Equation 1}$$

wherein,
Fe = the "enrichment factor"
Cp = the "pigment(s) content (wt %)" in the colorant sample
Cs = the "pigment(s) content (wt %)" in the source material
Np = the "nutritive constituents content (% wt)" in the colorant sample [i.e. sum % wt of total carbohydrates, fibres, proteins, and lipids in said sample]
Ns = the "nutritive constituents content (% wt)" in the source material [i.e. sum % wt of total carbohydrates, fibres, proteins, and lipids in said source material]

The below exemplifies how the enrichment factor is calculated for a given coloring agent.

|  | Carrot (% wt on a dry weight basis) | Carrot colorant A (% wt on a dry weight basis) | Carrot colorant B (% wt on a dry weight basis) |
|---|---|---|---|
| Carbohydrates | 40 | 45 | 0 |
| Fibres | 10 | 5 | 0 |
| Proteins | 10 | 12 | 14 |
| Lipids | 2 | 5 | 20 |
| Pigment | 0.1 | 0.3 | 4 |

Carrot colorant A [carrot concentrate]:

$$Fe = \frac{0.3 \div (45 + 5 + 12 + 5)}{0.1 \div (40 + 10 + 10 + 2)} \approx 3$$

Carrot colorant B [carrot extracted pigment]:

$$Fe = \frac{4 \div (14 + 20)}{0.1 \div (40 + 10 + 10 + 2)} \approx 73$$

EXAMPLES

Example 1: Aqueous Composition for the Manufacture of Hydroxypropyl Methyl Cellulose Hard Capsules with Hydrophilic Coloring Foodstuff Concentrate of Spirulina A 5 kg composition of 18.8% HPMC type 2906 (methoxy content 28.7%, hydroxypropoxy content 5.4%) of 4.4 cPs viscosity at 2% concentration (w/w) was prepared as follows:

The HPMC powder is dispersed into hot water at 75° C. under stirring. Formation of foam is observed. After complete dispersion of the powder, the temperature is kept at 75° C. under very gentle stirring for de-foaming of the dispersion. Then the dispersion is cooled down to 10° C. under gentle stirring for obtaining dissolution of the HPMC. After keeping the composition for more than 30 minutes at 10° C., the temperature is increased to about 25° C. at which point the hydrophilic coloring foodstuff concentrate of spirulina (1% w/w) [with Fe of about 4.5] is then directly added to the HPMC aqueous composition, and a dipping composition ready for use in capsule manufacturing is obtained.

A dip-molding process as described herein is then followed for generating hard capsules by dipping pre-heated mold pins (at a temperature of about 60° C.) into the dipping composition.

The HPMC composition gelling temperature is determined by viscosity measurement by progressively heating the composition. The gelling temperature is about 34° C.

Example 2: Aqueous Composition for the Manufacture of Hydroxypropyl Methyl Cellulose Hard Capsules with Hydrophilic Coloring Foodstuff Concentrate of Purple Carrot Example 1 is repeated but this time replacing the 1% w/w of spirulina with purple carrot concentrate [with Fe of about 3].

Example 3: Aqueous Composition for the Manufacture of Hydroxypropyl Methyl Cellulose Hard Capsules with Hydrophilic Coloring Foodstuff Concentrate of Safflower Example 1 is repeated but this time replacing the 1% w/w of spirulina with safflower concentrate [with Fe of about 5].

Example 4: Aqueous Composition for the Manufacture of Hydroxypropyl Methyl Cellulose Hard Capsules with Hydrophilic Coloring Foodstuff Concentrate of Sweet Potato Example 1 is repeated but this time replacing the 1% w/w of spirulina with sweet potato concentrate [with Fe of about 4].

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm" (i.e. every value in a practical range close to 40 mm).

The invention claimed is:
1. A two-piece hard capsule shell comprising:
a film forming capsule base material; and
a colorant, wherein the colorant consists of a hydrophilic coloring foodstuff concentrate having an enrichment factor of less than 6, and wherein the hydrophilic coloring foodstuff concentrate is present in an amount from about 0.001 wt % to about 5 wt % based on the empty hard capsule weight.
2. The two-piece hard capsule shell according to claim 1 wherein the film forming capsule base material comprises one or more celluloses, gelatin, pullulan, or any combination thereof.
3. The two-piece hard capsule shell according to claim 1 wherein the film forming capsule base material comprises one or more celluloses.
4. The two-piece hard capsule shell according to claim 1 wherein the film forming capsule base material comprises hydroxypropyl methyl cellulose (HPMC), hydroxypropyl methyl cellulose acetate succinate (HPMCAS), hydroxypropyl methyl cellulose phthalate (HPMCP), or methylcellulose (MC).
5. The two-piece hard capsule shell according to claim 1 wherein the film forming capsule base material comprises HPMC.
6. The two-piece hard capsule shell according to claim 1, further comprising a plasticizer, an antibacterial agent, a flavouring agent, or any combination thereof.
7. A dip-molding process for making a two-piece hard capsule shell comprising:
providing an aqueous composition comprising a film forming capsule base material;
mixing a colorant with the aqueous composition to provide a dipping composition, the colorant consisting of a hydrophilic coloring foodstuff concentrate having an enrichment factor of less than 6;
dipping one or more mold pins in the dipping composition;
extracting the one or more mold pins from the dipping composition such that a film is formed over the pins; and
drying the film to provide a two-piece hard capsule shell comprising the colorant in an amount from about 0.001 wt % to about 5 wt % based on the empty hard capsule shell weight.
8. The dip-molding process according to claim 7, wherein the aqueous composition is maintained at a temperature of from 25° C. to 45° C.
9. The dip-molding process according to claim 7, wherein the aqueous composition and the dipping composition have a pH of less than 6.
10. The dip-molding process according to claim 7, wherein the mold pins are pre-heated to a temperature that is greater than a gelation temperature of the dipping composition prior to dipping the one or more mold pins in the dipping composition.
11. The dip-molding process according to claim 10, wherein the dipping composition is maintained at a temperature of 1° C. to 10° C. below the gelation temperature of the dipping composition when dipping the one or more mold pins in the dipping composition.
12. The dip-molding process according to claim 7, wherein drying is performed at a temperature of less than 65° C.
13. The dip-molding process according to claim 7, wherein the film forming capsule base material comprises one or more celluloses, gelatin, pullulan, or any combination thereof.
14. The dip-molding process according to claim 7, wherein the film forming capsule base material comprises hydroxypropyl methylcellulose (HPMC).
15. The dip-molding process according to claim 14, wherein:
(i) the HPMC is a HPMC having a viscosity of 4.0 to 5.0 cPs as a 2% w/w solution in water at 20° C.; or
(ii) a concentration of the HPMC in the aqueous composition provides a viscosity of 1000 to 3000 cPs measured at a temperature of from 10° C. to 1° C. below a gelling temperature of the aqueous composition; or
(iii) both (i) and (ii).
16. The dip-molding process according to claim 7, wherein the two-piece hard capsule shell comprises the film forming capsule base material in an amount from about 80 wt % to about 99 wt %.
17. The dip-molding process according to claim 7, wherein the two-piece hard capsule shell comprises water in an amount from about 1 wt % to about 8 wt %.
18. The dip-molding process according to claim 7, wherein the hydrophilic coloring foodstuff concentrate is a concentrate of purple carrot, pumpkin, yam, radish, sweet potato, beetroot, elderberry, blackcurrant, grape, apple, huito, safflower, carthamus, hibiscus, tropaeolum, spirulina, chlorella, or any mixture thereof.

19. A two-piece hard capsule shell comprising:
a film forming capsule base material; and
a colorant,
wherein the colorant consists of a hydrophilic coloring foodstuff concentrate having an enrichment factor of less than 6,
the hydrophilic coloring foodstuff concentrate is present in an amount from about 0.001 wt % to about 5 wt % based on the empty hard capsule weight, and
the hydrophilic coloring foodstuff concentrate is a concentrate of purple carrot, pumpkin, yam, radish, sweet potato, elderberry, blackcurrant, grape, apple, huito, safflower, carthamus, hibiscus, tropaeolum, spirulina, chlorella, or any mixture thereof.

20. A two-piece hard capsule shell comprising:
a film forming capsule base material; and
a colorant,
wherein the colorant consists of a hydrophilic coloring foodstuff concentrate having an enrichment factor of less than 6, and
the hydrophilic coloring foodstuff concentrate is a concentrate of purple carrot, pumpkin, yam, radish, sweet potato, elderberry, blackcurrant, grape, apple, huito, safflower, carthamus, hibiscus, tropaeolum, spirulina, chlorella, or any mixture thereof.

* * * * *